(12) United States Patent
Wang

(10) Patent No.: US 12,270,460 B2
(45) Date of Patent: Apr. 8, 2025

(54) PULLEY AND STRUCTURE HAVING THE SAME CONNECTED WITH DRIVEN UNIT

(71) Applicant: CORNERSTONE TECHNOLOGY (SHENZHEN) LIMITED, Shenzhen (CN)

(72) Inventor: Zerui Wang, Shenzhen (CN)

(73) Assignee: CORNERSTONE TECHNOLOGY (SHENZHEN) LIMITED, Shenzhen (CN)

( * ) Notice: Subject to any disclaimer, the term of this patent is extended or adjusted under 35 U.S.C. 154(b) by 301 days.

(21) Appl. No.: 17/941,879

(22) Filed: Sep. 9, 2022

(65) Prior Publication Data
US 2023/0003286 A1    Jan. 5, 2023

Related U.S. Application Data

(63) Continuation of application No. PCT/CN2021/125032, filed on Oct. 20, 2021.

(30) Foreign Application Priority Data

Dec. 2, 2020    (CN) .......................... 202011402465.1

(51) Int. Cl.
*F16H 19/08*    (2006.01)
*A61B 34/00*    (2016.01)
(Continued)

(52) U.S. Cl.
CPC ............. *F16H 19/08* (2013.01); *A61B 34/30* (2016.02); *A61B 34/71* (2016.02); *B25J 9/104* (2013.01);
(Continued)

(58) Field of Classification Search
CPC .... F16H 19/08; F16H 55/36; F16H 2019/085; F16H 7/18; F16H 55/46; F16H 7/02;
(Continued)

(56) References Cited

U.S. PATENT DOCUMENTS 6,131,728 A     10/2000   Rizhanovsky
8,196,492 B1 *   6/2012   Denu ........................ B25J 9/042
                                                                414/744.5
(Continued)

FOREIGN PATENT DOCUMENTS

CN        2145776 Y      11/1993
CN        1847698 A      10/2006
(Continued)

OTHER PUBLICATIONS

English Translation of CN-113685516-A (Year: 2021).*
(Continued)

*Primary Examiner* — Victor L MacArthur
(74) *Attorney, Agent, or Firm* — ScienBiziP, P.C.

(57) ABSTRACT

A pulley and a structure having the pulley connected with a driven unit are provided. The pulley includes a wheel portion and a lug portion. The wheel portion includes two circular end surfaces opposing each other and a side surface connecting the two end surfaces. The side surface includes a main arc face and a branch arc face. The branch arc face has a head end connected to the main arc face and a tail end configured to connect a strap. The branch arc face has a width in an axial direction of the wheel portion smaller than a width of the main arc face. The lug portion is fixed to the wheel portion, disposed at a position adjacent to the branch arc face along the width of the main arc face and extends to protrude beyond the branch arc face in a radial direction of the wheel portion.

20 Claims, 5 Drawing Sheets

(51) Int. Cl.
*A61B 34/30* (2016.01)
*B25J 9/10* (2006.01)
*F16C 11/04* (2006.01)
*F16H 55/36* (2006.01)
*F16H 19/06* (2006.01)

(52) U.S. Cl.
CPC .............. *F16C 11/04* (2013.01); *F16H 55/36* (2013.01); *F16H 2019/0668* (2013.01); *F16H 2019/0677* (2013.01); *F16H 2019/085* (2013.01)

(58) Field of Classification Search
CPC ......... A61B 34/30; A61B 34/71; A61B 90/50; A61B 2017/00477; A61B 34/70; B25J 9/104; F16C 11/04; F16C 11/045; F16C 2316/10; F16C 2322/59
See application file for complete search history.

(56) References Cited

U.S. PATENT DOCUMENTS

| | | | |
|---|---|---|---|
| 10,595,948 B2* | 3/2020 | Solomon | A61B 34/37 |
| 10,646,292 B2* | 5/2020 | Solomon | A61B 34/37 |
| 2002/0133173 A1 | 9/2002 | Brock et al. | |
| 2007/0089557 A1 | 4/2007 | Solomon et al. | |
| 2008/0021440 A1* | 1/2008 | Solomon | A61B 34/37 |
| | | | 606/1 |
| 2013/0239735 A1* | 9/2013 | Solomon | A61B 34/71 |
| | | | 901/21 |
| 2015/0250549 A1* | 9/2015 | Solomon | A61B 34/30 |
| | | | 606/130 |
| 2016/0327138 A1* | 11/2016 | Mu | G02F 1/133528 |
| 2017/0143425 A9* | 5/2017 | Solomon | B25J 9/1045 |
| 2018/0079074 A1* | 3/2018 | Devengenzo | F16H 19/0672 |
| 2018/0250085 A1 | 9/2018 | Simi et al. | |

FOREIGN PATENT DOCUMENTS

| | | | |
|---|---|---|---|
| CN | 206466927 U | | 9/2017 |
| CN | 107363825 A | | 11/2017 |
| CN | 207935217 U | | 10/2018 |
| CN | 211315000 U | | 8/2020 |
| CN | 211693400 U | | 10/2020 |
| CN | 112539256 A | | 3/2021 |
| CN | 112682483 A | | 4/2021 |
| CN | 214367554 U | | 10/2021 |
| CN | 113685516 A | * | 11/2021 |
| WO | 219118334 A1 | | 6/2019 |

OTHER PUBLICATIONS

Extended European Search Report dated Aug. 21, 2023 regarding Application No. 21899756.7.
International Search Report and written opinion dated Jan. 19, 2022 for PCT application No. PCT/CN2021/125032.
The First Examination Opinion Notice dated Nov. 14, 2024 for Chinese Application No. 202011507761.8.

* cited by examiner

PULLEY AND STRUCTURE HAVING THE SAME CONNECTED WITH DRIVEN UNIT

CROSS REFERENCE TO RELATED APPLICATIONS

The present disclosure is a continuation of PCT Application No. PCT/CN2021/125032, filed Oct. 20, 2021 which claims priority to Chinese patent application No. 202011402465.1, filed Dec. 2, 2020, each of which is incorporated by reference herein in its entirety.

TECHNICAL FIELD

The present disclosure relates to the field of connection structure for mechanical transmission units, and particularly to a connection structure between a robotic arm and an end effector of a surgical robot.

BACKGROUND

The medical microsurgical instrument is widely used in all kinds of surgeries due to its advantages of accurate positioning, stable operation, dexterity, wide working range, fearlessness of radiation and infection, etc. During the operation, a plurality of robotic arms are controlled to move above a patient's body, and then perform the operation through an aperture pre-opened on the patient's body.

In current, the surgical robot usually employs a strap drive train for movement (e.g., pitch and yaw) of the robotic arm. Multiple robotic arms may be involved during the operation and operate to tissue through the aperture pre-opened on the patient's body. It is generally desirable that the robotic arm has a size as small as possible to avoid interference between the multiple robotic arms within a limited space. Accordingly, the strap drive train disposed within the robotic arm is required to be as compact as possible.

SUMMARY

Embodiments of the present disclosure provides a pulley including a wheel portion and a lug portion. The wheel portion includes two circular end surfaces opposing each other and a side surface connecting the two end surfaces. The side surface includes a main arc face and a branch arc face. The branch arc face has a head end connected to the main arc face and a tail end configured to connect a strap. The branch arc face has a width in an axial direction of the wheel portion smaller than a width of the main arc face. The branch arc face and the main arc face form a continuous circular arc surface on which the strap rides. The lug portion is fixed to the wheel portion. The lug portion is disposed at a position adjacent to the branch arc face along the width of the main arc face and extends to protrude beyond the branch arc face in a radial direction of the wheel portion. The lug portion is configured to connect the pulley to a driven unit.

Embodiments of the present disclosure provides a structure including a driven unit and a pulley according to any one of the aforementioned embodiments. The pulley is connected to the driven unit through the lug portion.

BRIEF DESCRIPTION OF THE DRAWINGS

To illustrate the technical solutions according to the embodiments of the present disclosure more clearly, the accompanying drawings for describing the embodiments are introduced briefly in the following. It should be appreciated that the accompanying drawings in the following description are only some embodiments of the present disclosure, and those skilled in the art can derive other drawings from the accompanying drawings without creative efforts.

DETAILED DESCRIPTION

In the following description, several embodiments of the present disclosure are shown by example. It should be appreciated that other embodiments may be derived with changes in mechanical component, structure, electrical, and operation without departing from the spirit and scope of the present disclosure. The following detailed description is not intended to limit the present disclosure, and the scope of embodiments of the present disclosure is limited by the claims.

All directional indications (such as upper, lower, left, right, front, rear, etc.) in embodiments of the present disclosure are used only to explain relative positional relationships, motion situations, etc., between components under a particular posture (as shown in the drawings), and will change accordingly if the particular posture changes.

In that present disclosure, expressions concerning "first," "second," etc., are for descriptive purposes only and cannot be understood as indicating or implying their relative importance or implying the number of technical features indicated. Thus, features defined with "first," "second" may explicitly or implicitly include at least one of such features.

In that present disclosure, unless otherwise specified and defined, the terms "connect," "fix" and the like should be understood broadly, for example, the expression concerning "connect" may be referred to a fixed connection, a detachable connection, or an integral form, may be a mechanical connection or an electrical connection, may be a direct connection or an indirect connection with an intermediate component, may be a communication between interiors of two components or an interaction between two components. For those skilled in the art, the specific meaning of the above terms in the present disclosure may be understood by case.

In addition, the technical solutions in the various embodiments of the present disclosure may be combined with each other on the basis of practicability for those skilled in the art. The combination which causes conflicts should be considered as nonexistent and does not fall within the protection scope as claimed by the present disclosure.

Typically, for pitching movement of an end effector of the robotic arm, the end effector is fixed to a pulley at a joint which the end effector rotates about. The pulley is driven to rotate under control of a strap connected thereto and wrapping thereon and the end effector rotates with the pulley to complete the pitching movement.

Figure 1:
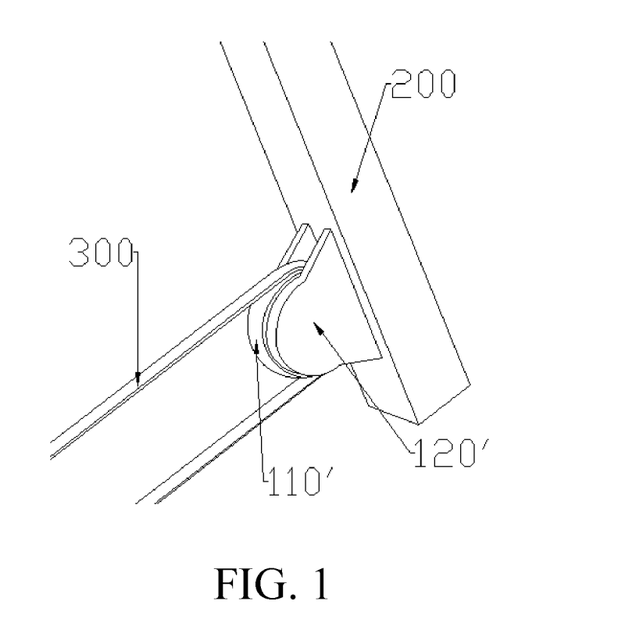
FIG. 1 is a schematic diagram showing a connection between a pulley and a driven unit in the existing design.
Figure 2:
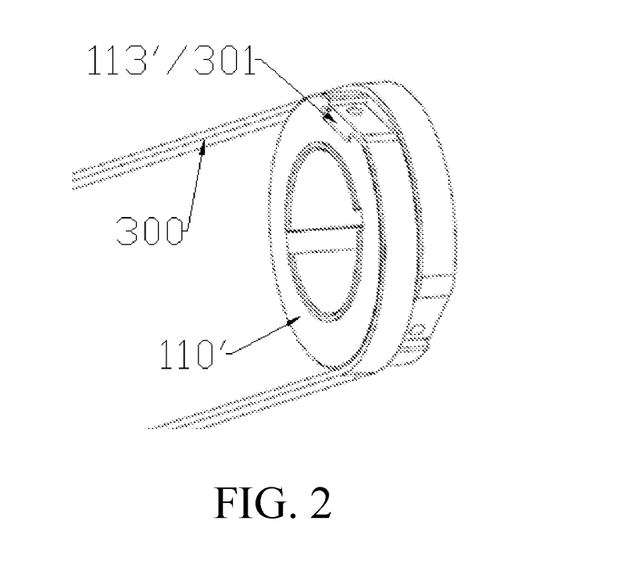
FIG. 2 is a schematic diagram showing a connection between the pulley and a strap in the existing design.

In a typical design, as show in FIG. 1, an inner lug 120' is provided on the end effector 200, and includes two tabs spaced from each other. The pulley 110' is sandwiched between the two tabs with both end surfaces of the pulley being fixed to the two tabs, respectively. The pulley 110' is hold by the two tabs and spaced from the end effector 200 for allowing straps 300 to wrap on the pulley 110'. FIG. 2, in which the inner lug 120' is omitted, shows how the straps 300 wraps on the pulley 110'. The straps 300 each has an end fixed to the pulley 110'. Then, the inner lug 120' together with the pulley 110' is inserted into an outer lug (not shown in FIG. 1) provided on a link of the robotic arm connected to the end effector 200. The inner lug 120' is pivotally connected to the outer lug by a pin to form the joint at which the end effector 200 and the link are connected. Thus, the thickness of the joint in the typical design is at least the sum of the thicknesses of the pulley 110', the inner lug 120', and the outer lug, resulting in a large size of the joint.

Hence, it is necessary to reduce the size of the joint and meanwhile ensure the reliability of the connections at the joint (e.g., the connection between the pulley and the end effector, the connection between the strap and the pulley, etc.) for normal operation.

Figure 3:
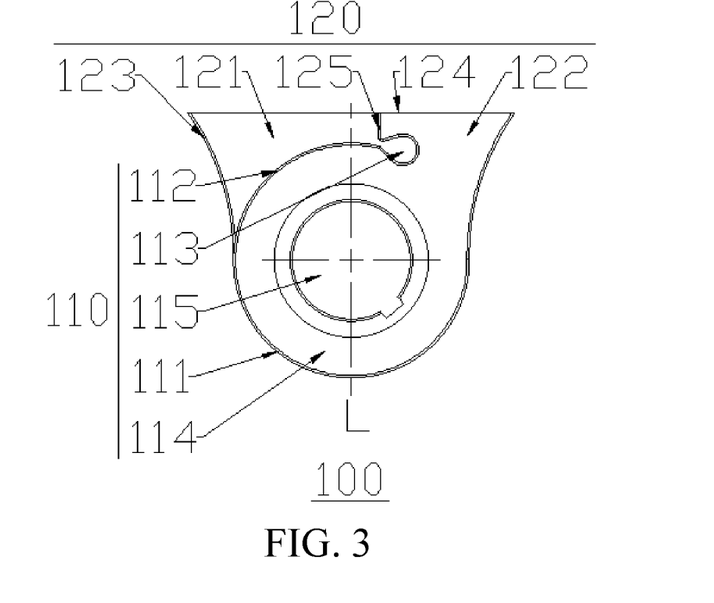
FIG. 3 is a front view of a pulley according to an embodiment of the present disclosure.
Figure 4:
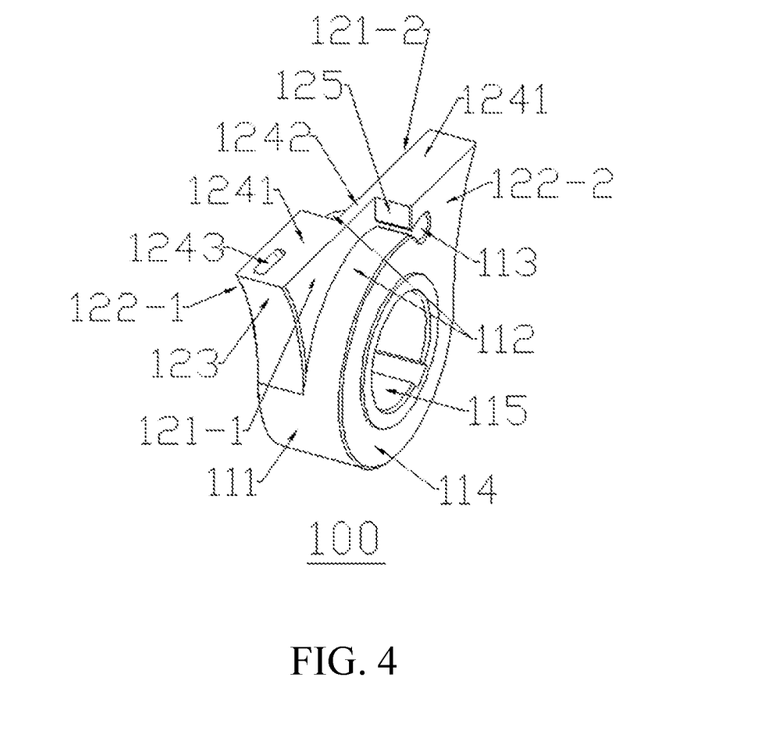
FIG. 4 is a perspective view of the pulley according to an embodiment of the present disclosure.
Figure 5:
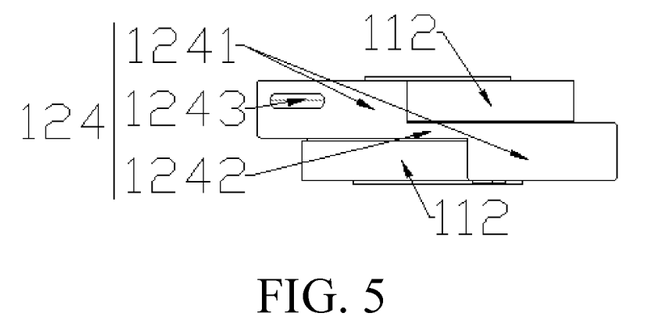
FIG. 5 is a top view of the pulley according to an embodiment of the present disclosure.

As shown in FIGS. 3-5, an embodiment of the present disclosure provides a pulley 100 including a wheel portion 110 and a lug portion 120. The wheel portion 110 is substantially cylindrical and includes two opposite circular end surfaces 114 and a side surface connecting the two circular end surfaces 114. The side surface includes a main arc face 111 and at least one branch arc face 112. The branch arc face 112 has a head end connected to the main arc face 111. In an axial direction of the wheel portion, the branch arc face 112 has a width smaller than that of the main arc face 111, The branch arc face 112 and the main arc face 111 form a continuous circular arc surface. The lug portion 120 is fixed to the wheel portion 110 and is disposed at a position adjacent to the branch arc face 112 along the width of the main arc face 111 and extends to protrude beyond the branch arc face 112 in a radial direction of the wheel portion 110.

Figure 8:
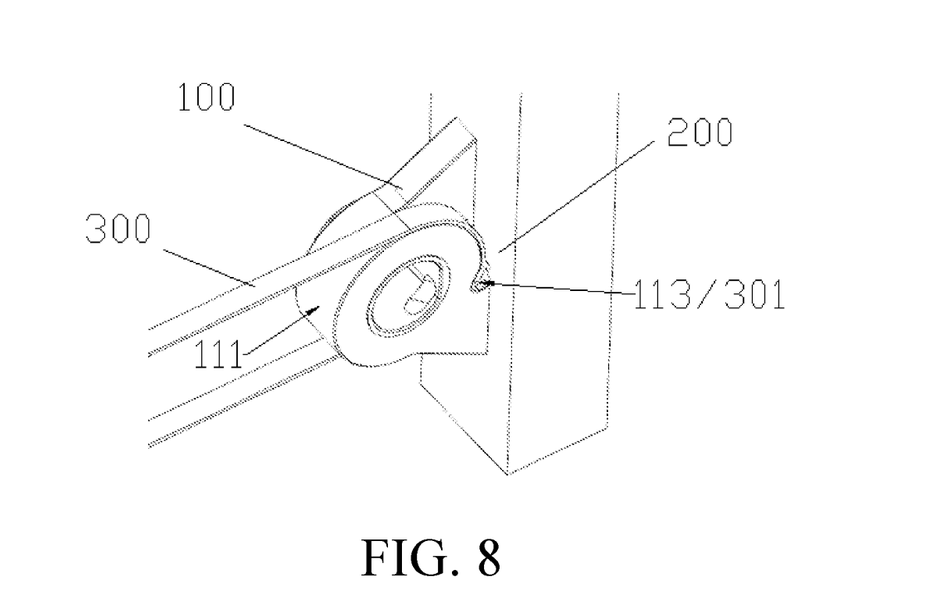
FIG. 8 is a partial view of the structure with a strap mounted thereto according to an embodiment of the present disclosure.

Further referring to FIG. 8, in the pulley 100, the branch arc face 112 further includes a tail end configured to connect a strap 300 which rides on the continuous circular arc surface formed by the branch arc face 112 and the main arc face 111. The lug portion 120 is configured to connect the pulley 100 to a driven unit 200.

In this embodiment, the main arcuate surface 111 and the branch arc face 112 forms the continuous circular arc surface for wrapping of the strap 300. Compared with the typical pulley which is merely shaped as a wheel, the pulley according to the embodiment of the present disclosure includes, not only the wheel portion 11 which is substantially cylindrical and has the main arcuate surface 111 and the branch arc face 112, but also the lug portion 120 which protrudes from the wheel portion 11 and configured to be fixed to the driven unit. Compared with the existing technology, the present disclosure provides an integrally formed pulley which is simpler in structure, in which the wheel portion 110 is improved for wrapping of the strap 300 and an additional lug portion 120 is provided on the wheel portion 110, the pulley is fixed to the driven unit 200 through the lug portion 120 integrally formed with the wheel portion 110, so that components such as the tabs 120' of the inner lug as shown in FIG. 1 can be omitted. In this way, the thickness of the connection of the pulley 100 is reduced, and a compact structure including the pulley 100 and the driven unit 200 is achieved, resulting in a smaller size and a lower weight of the robotic arm and thus improving operative accuracy during the surgeries.

In an embodiment, the lug portion 120 includes a first end surface 121 adjacent to and perpendicular to the branch arc face 112, a second end surface 122 opposite to the first end surface 121, a first side surface 123 connecting the first end surface 121 and the second end surface 122 and extending from the main arc face 111, a top surface 124 connecting the first end surface 121 and the second end surface 122 and disposed at a top of the pulley 100, and a second side surface 125 disposed above the branch arc face 112 and connecting the top surface 124. The top surface 124 is, for example, flat and is configured to be attached to a surface (for example, which is also flat) of the driven unit 200, so that the pulley 100 is fixed to the driven unit 200. As an example, the top surface 124 is fixed to the flat surface of a main arm of the driven unit 200 by mechanical connection or welding, or is integrally formed with the main arm of the driven unit 200.

In this embodiment, with the reasonable design of the lug portion 120, the pulley 100 is connected to the driven unit 200 through the connection of two flat surfaces. While in the existing technology, the connection between the pulley and the driven unit is realized by inserting the pulley between tabs of the driven unit, which may become loose during a long-term operation. The solution provided in the embodiment of the present disclosure avoids such problems during the long-term operation, and thus improves the reliability.

In an embodiment, a connector chamber 113 is provided at the tail end of the branch arc face 112 and configured to receive and hold a strap connector 301 which is connected to the strap 300. For example, the strap connector 301 is matched in shape with the connector chamber 113. The connector chamber 113 may be located in the wheel portion 110, or in the lug portion 120, or at a position where the wheel portion 110 and the lug portion 120 connected. The connector chamber 113 includes an abdomen and a mouth sized smaller than the abdomen, and the mouth opens to the branch arc face 112. In a specific application, the strap connector 301 is received in the connector chamber 113, and the strap 300 extends out of the connector chamber 113 through the mouth and further extends along and rides on the branch arc face 112.

In this embodiment, the connector chamber 113 with a large abdomen and a small mouth is provided to connect the strap connector 301 without requiring any additional fastener such as screws, which simplifies the connection of the strap connector, and contributes to the reasonable design of the lug portion 120 on the wheel portion 110.

In an embodiment, the mouth of the connector chamber 113 has a top connecting the second side surface 125, and the top surface 124 is disposed above the connector chamber 113 and spaced from the connector chamber 113. In this way, with such a simple structure, it is effectively ensured that no interference occurs between the strap connector and the robotic arm or the driven unit 200 during operation.

In an embodiment, the pulley 100 is rotated-symmetrical about the radial direction of the wheel portion 110 (i.e., the broken line L as shown in FIG. 3). Each of the left and right sides of the pulley 100 includes a branch arc face 112, a connector chamber 113 and a lug portion 120, so that the two straps 300 are connected to the pulley and run in opposite directions. Specifically, the first end surfaces 121 (i.e., a first end surface 121-1 on the left and a first end surface 121-2 on the right as shown in FIG. 4), the second end surfaces 122 (i.e., a second end surface 122-1 on the left and a second end surface 122-2 on the right as shown in FIG. 4) and the second side surfaces 125 (not indicated with separate reference numerals) of the two lug portions 120 are also rotated-symmetrical. The rotated-symmetrical structure makes it possible to connect the straps 300 at both sides.

In an embodiment, each of the two branch arc faces 112 has a central angle larger than 90°, so that the pulley 100 is driven by the straps 300 to rotate both clockwise and anticlockwise by over 90°. In an embodiment, the main arc face 111 has a central angle of 180°. The width of each of the two branch arc faces 112 is half that of the main arc face 111. Alternatively, the width of each of the two branch arc faces 112 may be less than a half of the width of the main arc face 111. The two branch arc faces 112 partly overlap in the axial direction of the wheel portion 110 and share the main arc face 111. In this way, the wheel portion 110 has a simple structure. In an embodiment, the first side surface 123 of the lug portion 120 transitions smoothly to the main arc face 111 and extends in a direction away from the main arc face 111 to be lifted from a plane that is tangent to the main arc face 111 at the connection between the main arc face 111 and the first side surface 123. In this way, the pulley 100 has a smooth outline, and the connection area between the pulley 100 and the driven unit 200 is increased. In an embodiment, the top surface 124 includes a main connection surface 1241 on each side and an intermediate connection surface 1242 connecting the main connection surfaces 1241. In an embodiment, a wiring hole 1243 is provided and opens at the top surface 124 for allowing wires to pass therethrough and enter the driven unit 200. The wiring hole 1243 penetrates through an inner wall of the wheel portion 110 to communicate a mounting hole 115 defined by the inner wall. In an embodiment, the mounting hole 115 penetrates through the two circular end surfaces in the axial direction of the wheel portion 110. The mounting hole 115 allows a rotary shaft of the robotic arm to be inserted therein.

In the above embodiments, with cooperation of the lug portion 120 and the connector, the pulley 100 can achieve the connection between the connector and the lug portion 120 and the normal wrapping of the strap, and the driven unit 200 is rotatable by a large angle with driven of the pulley 100. Meanwhile, the thickness of the robotic arm is reduced and the reliability of the connection between the robotic arm and the end effector is ensured. Further, no interference with the robotic arm occurs in the subsequent installation.

Figure 6:
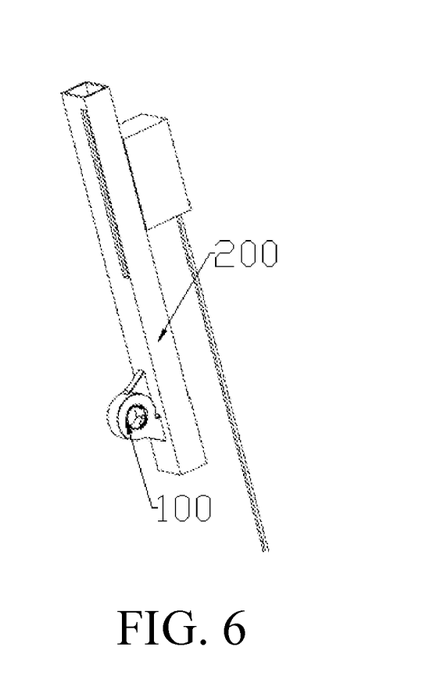
FIG. 6 is a schematic diagram of a structure having a pulley and a driven unit connected with each other according to an embodiment of the present disclosure.
Figure 7:
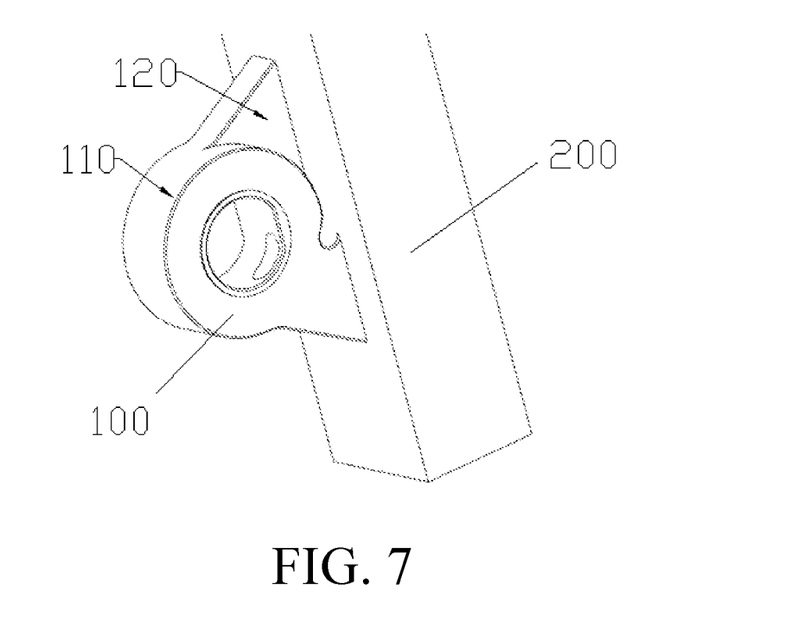
FIG. 7 is a partial view of the structure according to an embodiment of the present disclosure.
Figure 9:
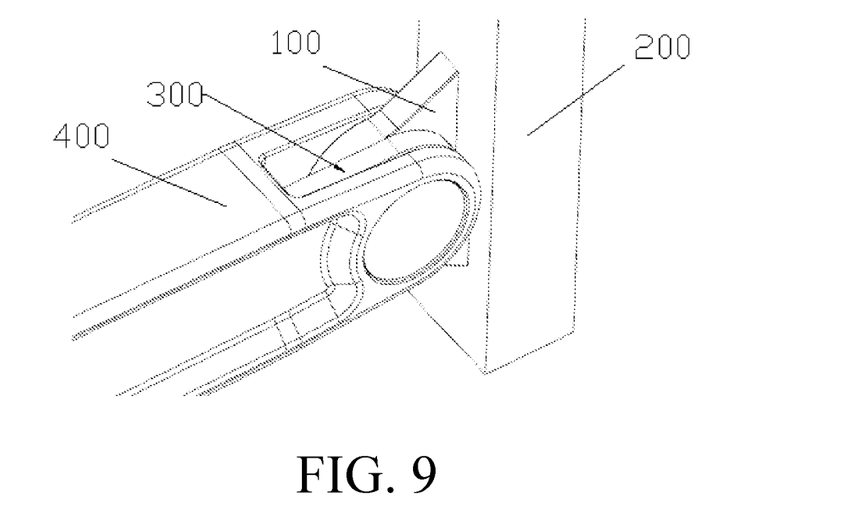
FIG. 9 is a partial view of the structure connected to a link of a robotic arm according to an embodiment of the present disclosure.
Figure 10:
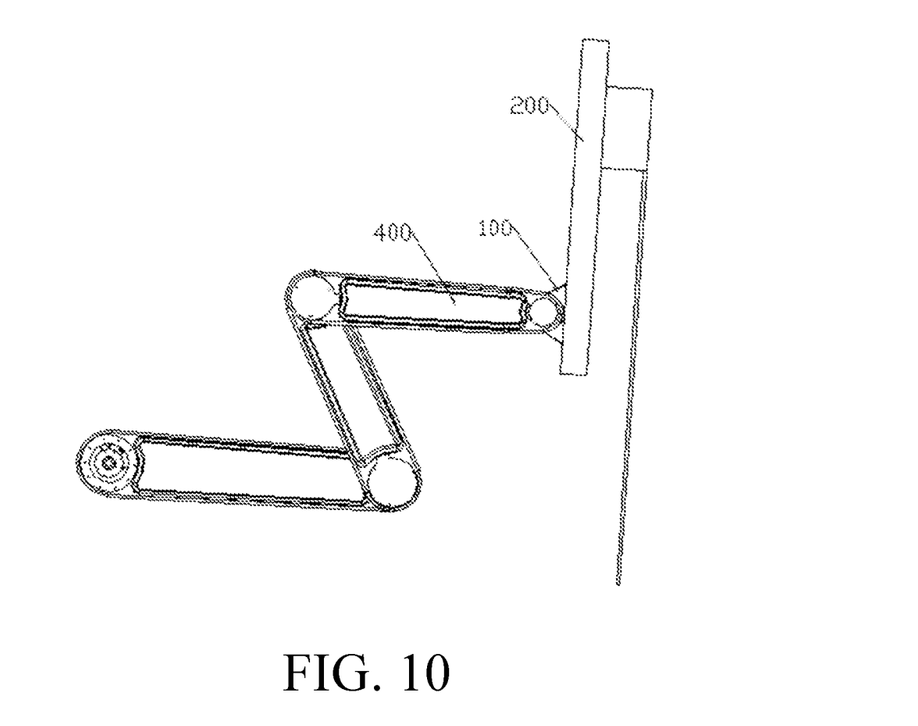
FIG. 10 is a schematic diagram of a robotic arm having the structure according to an embodiment of the present disclosure.

As shown in FIGS. 6-9, an embodiment of the present disclosure provides a structure including a pulley and a driven unit connected to each other. The pulley 100 is connected to the driven unit 200 through the lug portion 120. For example, the lug portion 120 is fixed to the driven unit 200 by mechanical connection or welding, or is integrally formed with the driven unit 200. For example, the top surface 124 of the lug portion 120 is attached to a flat surface of the driven unit 200. The driven unit 200 may be an end effector for a robotic arm, particularly an end instrument holder of a surgical robot. The strap connector 301 at the end of the strap 300 is held in the connector chamber 113 below the top surface 124, and the second side surface 125 provides a safe distance for avoiding interference between the strap connector and the driven unit 200. The pulley 100 is fixed to the driven unit 200 as shown in FIGS. 6 and 7, and then the strap connector 301 is inserted into the connector chamber 113 as shown in FIG. 8, and then a rotary shaft is inserted into the mounting hole 115, and the pulley 100 is sandwiched by the robotic arm housing 400, as shown in FIG. 9. As shown in FIG. 10, an embodiment of the present disclosure provides a robotic arm having the structure. The robotic arm may be used in a surgical robot.

In this structure, the connection of the driven unit 200 and the pulley 100 are "half-connected," that is, two straps 300 each wraps about a half of the pulley 100 on the left side or right side, and the lug portion 120 without strap 300 wrapping thereon is connected to the driven unit 200. In this way, the thickness of the connection is greatly reduced as the tabs of the end effector used in the existing surgical robot is omitted, resulting in a reduced thickness of the end link of the robotic arm and a compact connection with higher rigidity.

In FIG. 7, the pulley is rotated-symmetrical about the radial direction of the wheel portion 110 with being hollowed at the front upper left and the rear upper right, or at the front upper right and the rear upper left. The straps 300 are connected to the lug portion and extend to ride on the wheel portion within the hollows. In this way, the thickness of the link of the robotic arm is greatly reduced. The rigidity of connection is increased as the connection area between the lug portions and the end effector.

In an embodiment, the strap 300 may include a steel strap, or other flexible transmission mechanisms such as belts, ropes, or the like. During running of the strap, the pulley rotates by less than a round. The lug portion for connection with the driven unit is disposed at a same level in the width of the pulley as the strap, resulting an improved efficiency in space utilization. Those having the same concept as the present disclosure are considered as variants to the embodiments of the present disclosure.

Compared with the related art, in the pulley 100 and the structure including the pulley 100 and the driven unit 200 connected to each other according to the embodiments of the present disclosure, a integrally formed pulley is provided with a simpler structure, in which the wheel portion 110 is improved for wrapping of the strap 300 and an additional lug portion 120 is provided on the wheel portion 110, the pulley 100 is fixed to the driven unit 200 through the lug portion 120 integrally formed with the wheel portion 110, so that components such as the tabs 120' of the inner lug as shown in FIG. 1 can be omitted. In this way, the thickness of the connection of the pulley 100 is reduced, and a compact structure including the pulley 100 and the driven unit 200 is achieved, resulting in a smaller size and a lower weight of the robotic arm and thus improving operative accuracy during the surgeries.

The description above is merely some embodiments of the present disclosure, and is not intended to limit the scope of the present disclosure. Any equivalent structural transformation made using the contents of the specification and drawings of the present disclosure or applied in other related technical fields under the concept of the present disclosure falls within the scope of the present disclosure.

The invention claimed is:

1. A pulley comprising:
   a wheel portion including two circular end surfaces opposing each other and a side surface connecting the two end surfaces, wherein the side surface includes a main arc face and a branch arc face, the branch arc face has a head end connected to the main arc face and a tail end configured to connect a strap, the branch arc face has a width in an axial direction of the wheel portion smaller than a width of the main arc face, and the branch arc face and the main arc face form a continuous circular arc surface on which the strap rides; and a lug portion fixed to the wheel portion, wherein the lug portion protrudes from the side surface in a radial direction of the wheel portion and is aligned with the branch arc face in a circumferential direction of the wheel portion, and the lug portion is configured to connect the pulley to a driven unit.

2. The pulley according to claim 1, wherein the lug portion includes a first end surface adjacent to and perpendicular to the branch arc face, a second end surface opposite to the first end surface and flush with one of the end surfaces of the wheel portion, a first side surface connecting the first end surface and the second end surface and extending from the main arc face, a top surface connecting the first end surface and the second end surface and disposed at a top of the pulley, and a second side surface disposed above the branch arc face and connecting the top surface, and the top surface is configured to be attached to a surface of the driven unit.

3. The pulley according to claim 2, wherein a connector chamber is provided at the tail end of the branch arc face and configured to receive and hold a strap connector connected to the strap, and the connector chamber includes an inner wall transitioning between the tail end of the branch arc face and the second side surface of the lug portion.

4. The pulley according to claim 3, wherein the connector chamber includes an abdomen and a mouth sized smaller than the abdomen, and the mouth opens to the branch arc face.

5. The pulley according to claim 2, wherein the first side surface of the lug portion transitions smoothly to the main arc face and extends in a direction away from the main arc face to be lifted from a plane that is tangent to the main arc face at the connection between the main arc face and the first side surface.

6. The pulley according to claim 1, comprising two branch arc faces, two connector chambers and two lug portions, wherein the pulley is rotated-symmetrical about the radial direction of the wheel portion.

7. The pulley according to claim 6, wherein each of the two branch arc faces has a central angle larger than 90°.

8. The pulley according to claim 7, wherein the main arc face has a central angle of 180°, the width of each of the two branch arc faces is less than or equal to a half of the width of the main arc face, the two branch arc faces partly overlap in the axial direction of the wheel portion and share the main arc face.

9. The pulley according to claim 6, wherein the width of each of the two branch arc faces is less than a half of the width of the main arc face, the top surface includes two main connection surfaces disposed above the two connector chambers respectively and an intermediate connection surface connecting the two main connection surfaces.

10. The pulley according to claim 1, wherein the wheel portion is ring-shaped with an inner wall defining a mounting hole, the mounting hole penetrates through the two end surfaces in the axial direction of the wheel portion.

11. The pulley according to claim 10, wherein a wiring hole is provided, the wiring hole opens at a surface of the lug portion connected to the driven unit and penetrates through the inner wall of the wheel portion to communicate the mounting hole, the wiring hole is configured to allow wires to pass therethrough and enter the driven unit.

12. The pulley according to claim 1, wherein the lug portion is disposed between the main arc face and the branch arc face in the circumferential direction.

13. The pulley according to claim 1, wherein the lug portion defines a connector chamber configured to receive and hold a strap connector connected to the strap, the connector chamber includes an inner wall connecting to the tail end of the branch arc face.

14. The pulley according to claim 1, comprising a first lug portion and a second lug portion having an offset to the first lug portion in the circumferential direction, the wheel portion includes a first branch arc face and a second branch arc face, the first branch arc face is aligned with the first lug portion in the circumferential direction and adjacent to second part in the axial direction, and the second strap is aligned with the second lug portion in the circumferential direction and adjacent to first lug portion in the axial direction.

15. A structure comprising a driven unit and a pulley, wherein the pulley includes:

a wheel portion including two circular end surfaces opposing each other and a side surface connecting the two end surfaces, wherein the side surface includes a main arc face and a branch arc face, the branch arc face has a head end connected to the main arc face and a tail end configured to connect a strap, the branch arc face has a width in an axial direction of the wheel portion smaller than a width of the main arc face, and the branch arc face and the main arc face form a continuous circular arc surface on which the strap rides; and a lug portion fixed to the wheel portion, wherein the lug portion protrudes from the side surface in a radial direction of the wheel portion and is aligned with the branch arc face in a circumferential direction of the wheel portion, and the lug portion connects the pulley to the driven unit.

16. The structure according to claim 15, wherein the driven unit is an end effector for a robotic arm.

17. A strap drive train comprising:

a pulley including:

a wheel portion including two circular end surfaces opposing each other and a side surface connecting the two end surfaces, wherein the side surface includes a main arc face and a branch arc face, the branch arc face has a head end connected to the main arc face and a tail end configured to connect a strap, the branch arc face has a width in an axial direction of the wheel portion smaller than a width of the main arc face, and the branch arc face and the main arc face form a continuous circular arc surface on which the strap rides, and a lug portion fixed to the wheel portion, wherein the lug portion protrudes from the side surface in a radial direction of the wheel portion and is aligned with the branch arc face in a circumferential direction of the wheel portion, and the lug portion is configured to connect the pulley to a driven unit; and at least one strap connected to the pulley and riding on the side surface.

18. The strap drive train according to claim 17, wherein the lug portion defines at least one chamber, each of the at least one strap is connected to a strap connector which is received in a respective one of the at least one chamber.

19. The strap drive train according to claim 17, wherein the lug portion includes a first part and a second part having an offset to the first part in a circumferential direction of the wheel portion, the at least one strap includes a first strap and a second strap, the first strap is connected to the first part and adjacent to second part in an axial direction of the wheel portion, and the second strap is connected to the second part and adjacent to first part in the axial direction.

20. The strap drive train according to claim 17, the at least one strap is aligned with the lug portion in a circumferential direction of the wheel portion.

* * * * *